United States Patent
Diseroad

(10) Patent No.: US 8,530,665 B2
(45) Date of Patent: Sep. 10, 2013

(54) CRYSTALLINE (R)-(E)-2-(4-(2-(5-(1-(3,5-DICHLOROPYRIDIN-4-YL)ETHOXY)-1H-INDAZOL-3-YL)VINYL)-1H-PYRAZOL-1-YL)ETHANOL

(75) Inventor: Benjamin Alan Diseroad, Martinsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 32 days.

(21) Appl. No.: 13/248,055

(22) Filed: Sep. 29, 2011

(65) Prior Publication Data

US 2012/0083511 A1 Apr. 5, 2012

Related U.S. Application Data

(60) Provisional application No. 61/389,911, filed on Oct. 5, 2010.

(51) Int. Cl.
*C07D 213/00* (2006.01)
*A61K 31/44* (2006.01)

(52) U.S. Cl.
USPC .......................................... 546/339; 514/338

(58) Field of Classification Search
None
See application file for complete search history.

(56) References Cited

U.S. PATENT DOCUMENTS 7,429,609 B2 9/2008 Ohi et al.
8,268,869 B2 * 9/2012 Chen et al. ............... 514/338

FOREIGN PATENT DOCUMENTS

| WO | 02/10137 A2 | 2/2002 |
| WO | 02/22598 A1 | 3/2002 |
| WO | 2007/058626 A1 | 5/2007 |
| WO | 2010/129509 A1 | 11/2010 |

OTHER PUBLICATIONS

Ivanisevic, I., Pharm. Form. Qual. 2011, pp. 30-33.*
Brittain, H., ed Polymorphism in Pharmaceutical Solids 2009 pp. 318-335.*
Zhao, Genshi, et al., "A Novel, Selective FGFR Inhibitor That Causes Blockade of FGFR Autophosphorylation Shows a Broad-Spectrum of Anti-Tumor Activity in Preclinical Xenograft Tumor Models," poster presented at the AACR 101st Annual Meeting 2010, Apr. 17-21, 2010, Washington, D.C.

* cited by examiner

*Primary Examiner* — Janet Andres
*Assistant Examiner* — Heidi Reese
(74) *Attorney, Agent, or Firm* — Tina M. Tucker

(57) ABSTRACT

The present invention provides crystalline (R)-(E)-2-(4-(2-(5-(1-(3,5 -dichloropyridin-4-yl)ethoxy)-1H-indazol-3-yl)vinyl)-1H-pyrazol-1-yl)ethanol useful in the treatment of cancer.

9 Claims, No Drawings

CRYSTALLINE (R)-(E)-2-(4-(2-(5-(1-(3,5-DICHLOROPYRIDIN-4-YL)ETHOXY)-1H-INDAZOL-3-YL)VINYL)-1H-PYRAZOL-1-YL)ETHANOL

This application claims the benefit of U.S. Provisional Application No. 61/389,911, filed Oct. 5, 2010.

Fibroblast growth factor (FGF) has been recognized as an important mediator of many physiological processes, such as morphogenesis during development and angiogenesis. The fibroblast growth factor receptor (FGFR) family consists of four members (FGFR1-FGFR4), which are glycoproteins composed of extracellular immunoglobulin (Ig)-like domains, a hydrophobic transmembrane region and a cytoplasmic part containing a tyrosine kinase domain. FGF binding leads to FGFR dimerization, followed by receptor autophosphorylation and activation of downstream signaling pathways. Receptor activation is sufficient for the recruitment and activation of specific downstream signaling partners that participate in the regulation of diverse processes such as cell growth, cell metabolism and cell survival. Thus, the FGF/FGFR signaling pathway has pleiotropic effects on many biological processes critical to tumor cell proliferation, migration, invasion, and angiogenesis.

Vinyl indazoles are known in the art for the treatment of cancer. See for example, WO200210137 and WO2003101968. FGFR inhibitors are also known in the art. See for example, WO2002022598.

PCT/US2010/033487 discloses an amorphous form of (R)-(E)-2-(4-(2-(5-(1-(3,5-dichloropyridin-4-yl)ethoxy)-1H-indazol-3-yl)vinyl)-1H-pyrazol-1-yl)ethanol that is poorly crystalline and is useful as an inhibitor of FGFR.

The present invention provides a crystalline (R)-(E)-2-(4-(2-(5-(1-(3,5-dichloropyridin-4-yl)ethoxy)-1H-indazol-3-yl)vinyl)-1H-pyrazol-1-yl)ethanol that is a potent inhibitor of FGFR and may offer the advantageous properties relative to the prior form of superior solid handling properties on a large scale, ease of purification by crystallization, and thermodynamic stability under conditions of pharmaceutical processing and storage. In one embodiment, the crystalline (R)-(E)-2-(4-(2-(5-(1-(3,5-dichloropyridin-4-yl)ethoxy)-1H-indazol-3-yl)vinyl)-1H-pyrazol-1-yl)ethanol is the monohydrate form.

The present invention also provides crystalline (R)-(E)-2-(4-(2-(5-(1-(3,5-dichloropyridin-4-yl)ethoxy)-1H-indazol-3-yl)vinyl)-1H-pyrazol-1-yl)ethanol characterized by the X-ray powder diffraction pattern (Cu radiation, $\lambda=1.54059$ Å) comprising a peak at 14.65, and one or more peaks at 3.54, 12.51, or 19.16(2θ+/−0.1°).

The present invention provides a method of treating cancer wherein the cancer is selected from the group consisting of breast cancer, non-small cell lung (NSCL) cancer, bladder cancer, gastric cancer, pancreatic cancer, prostate cancer, colon cancer, multiple myeloma, liver cancer, melanoma, head and neck cancer, thyroid cancer, renal cell cancer, glioblastoma, and testicular cancer in a mammal comprising administering to a mammal in need of such treatment an effective amount of a compound or salt of the present invention.

This invention also provides pharmaceutical compositions comprising a compound or salt of the present invention in combination with one or more pharmaceutically acceptable carriers, diluents, or excipients. In a particular embodiment the composition further comprises one or more other therapeutic agents.

This invention also provides a compound or salt of the present invention for use in therapy. Additionally, this invention provides use of a compound or salt of the present invention in the manufacture of a medicament for treating cancer. Additionally, this invention provides for use of a compound or salt of the present invention for use in the treatment of cancer. In particular these cancers are selected from the group consisting of breast cancer, lung cancer, bladder cancer, gastric cancer, pancreatic cancer, prostate cancer, colon cancer, multiple myeloma AML, liver cancer, melanoma, head and neck cancer, thyroid cancer, renal cell cancer, glioblastoma, and testicular cancer. More particularly, the cancers are selected from the group consisting of breast cancer, non-small cell lung cancer, bladder cancer, gastric cancer, pancreatic cancer, prostate cancer, colon cancer, multiple myeloma, liver cancer, melanoma, head and neck cancer, thyroid cancer, renal cell cancer, glioblastoma, and testicular cancer. Most particularly the cancer is non-small cell lung cancer. Most particularly the cancer is gastric cancer. Most particularly the cancer is multiple myeloma. Furthermore, this invention provides a pharmaceutical composition for treating cancer selected from the group consisting of breast cancer, non-small cell lung cancer, bladder cancer, gastric cancer, pancreatic cancer, prostate cancer, colon cancer, multiple myeloma, liver cancer, melanoma, head and neck cancer, thyroid cancer, renal cell cancer, glioblastoma, and testicular cancer comprising a compound or salt of the present invention as an active ingredient.

It will be understood by the skilled reader that all of the compounds of the present invention are capable of forming salts. The compounds of the present invention are amines, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts", *Journal of Pharmaceutical Sciences*, Vol 66, No. 1, January 1977.

As used herein, the term "isolated" means crystalline (R)-(E)-2-(4-(2-(5-(1-(3,5-dichloropyridin-4-yl)ethoxy)-1H-indazol-3-yl)vinyl)-1H-pyrazol-1-yl)ethanol that is 99% pure.

The compounds of the present invention can be prepared essentially as illustrated in the preparations and examples below. The naming of the following preparations and examples is done using the Struct=Name naming feature in ChemDraw® Ultra 10.0.

Preparation 1

1-(3,5-Dichloropyridin-4-yl)ethanol

To a 3-neck 12 L round bottom flask add tetrahydrofuran (THF, 3 L) and diisopropylamine (DIPA, 315 mL, 2.24 mol) and cool to −78° C. Add slowly n-butyllithium (1.6 M in hexanes, 1400 mL, 2.24 mol). After the addition is complete and the temperature has settled at −78° C. slowly add a solution of 3,5-dichloropyridine (296.7 g, 2.00 mol) which immediately forms a yellow solution that changes to a rust colored suspension. After the addition is complete and the temperature has settled at −78° C. slowly add acetaldehyde (230 mL, 4.05 mol) in THF (600 mL). Continue stirring at −78° C. After 3 hours, remove the dry ice bath and begin quenching the reaction by the dropwise addition of saturated aqueous ammonium chloride (1 L). Allow the reaction to warm to room temperature (RT) overnight with stirring. Dilute the mixture with methyl-tert-butylether (MTBE, 2 L), saturated aqueous ammonium chloride (1 L) and water (2 L). Partition and wash organics with saturated aqueous sodium chloride (brine). Extract the aqueous phase with MTBE (1.5 L). Combine the organic layers, dry over sodium sulfate, filter and concentrate in vacuo. Purify the residue by silica gel chromatography [25% ethylacetate (EA) in hexanes] to give the title compound as a red oil. Yield: 352 g (90%). MS (ES) m/z 192 [M+1]$^+$.

Preparation 2

(S)-1-(3,5-Dichloropyridin-4-yl)ethanol

Separate the mixture of stereoisomers obtained in Preparation 1 on a CHIRALPAK® AD-H column eluting with 90% heptanes/10% ethanol. Peak 2 is the desired enantiomer. To establish the absolute configuration dissolve a sample of the product in CDCl$_3$ (final concentration 100 mg/mL). Obtain the vibrational circular dichroism (VCD) and infra red (IR) spectra with a resolution of 4 cm-1 using a ChiralIR FT VCD spectrometer (BioTools Inc®) with an IR cell equipped with BaF$_2$ windows and a path length of 100 mm. Collect the VCD and IR for 6 hours with 150 μL of the sample. Present the data without smoothing or further data processing. Obtain vibrational frequencies and absorption and VCD intensities by optimizing the lowest energy conformer by Gaussian at the B3PW91/6-31 G** level on a Linux cluster, and simulate the corresponding spectra using a Lorentzian bandwidth of 6 cm-1 vibrational circular dichroism. The above analysis shows the product to be the S-isomer. Yield: 84.37 g (27%). MS (ES) m/z 192 [M+1]$^+$.

Preparation 3

(S)-1-(3,5-Dichloropyridin-4-yl)ethyl methanesulfonate

Dissolve (S)-1-(3,5-dichloropyridin-4-yl)ethanol (5.02 g, 26.14 mmol) in dichloromethane (DCM, 100 mL) and cool the flask in an ice bath. Add triethylamine (TEA, 3.5 mL, 25.11 mmol) followed by the dropwise addition of methanesulfonyl chloride (2.2 mL, 28.42 mmol). Remove the ice bath and allow the reaction to warm to RT. After 4 hours, quench the reaction with water (100 mL) and separate layers. Extract the aqueous layer with DCM (50 mL) followed by 20% isopropyl alcohol (IPA)/chloroform (50 mL). Combine the organic extracts, dry over anhydrous sodium sulfate, filter and concentrate in vacuo. Yield: 7.15 g, (100%). MS (ES) m/z 270 [M+1]$^+$.

Preparation 4

4-Iodo-1-(2-(tetrahydro-2H-pyran-2-yloxy)ethyl)-1H-pyrazole

In a 1 L 3-neck flask equipped with magnetic stir bar, nitrogen blanket and internal temperature probe dissolve 2-(2-bromoethoxy)tetrahydro-2H-pyran (34 g, 156 mmol) in acetonitrile (ACN, 400 mL). Add 4-iodopyrazole (29.34 g, 149.74 mmol) followed by cesium carbonate (73.4 g, 223.02 mmol). Stir the mixture at RT for 18 hours. Filter the reaction mixture through CELITE®, wash the filter cake with ACN and concentrate the filtrate to a golden oil. Use without further purification. Yield: 47.819 g (99%). MS (ES) m/z 323 [M+1]$^+$.

Preparation 5

5-(tert-Butyldimethylsilyloxy)-1H-indazole

Charge a 10 L reaction vessel with N,N-dimethylformamide (DMF, 2.50 L), 5-hydroxyindazole (150.20 g, 1.12 mol) and 1H-imidazole (114.35 g, 1.68 mol). Cool the mixture to 0° C. and add tert-butyldimethylchlorosilane (253.16 g, 1.68 mol) over 0.5 hours. Stir the mixture at 18° C. for 3 hours. Add water (2.5 L) to the reaction slowly with an ice bath at 5° C. to maintain an internal temperature at around 20° C. Transfer the mixture to a separating funnel and extract with EA (2×2.5 L). Combine the extracts and wash with water (3×2.5 L) and brine. Dry the organic solutions over anhydrous sodium sulfate, filter, and evaporate to a red oil. Pass the oil through a silica gel pad and elute with eluent (0% to 30% EA in hexane) to afford the title compound as an orange oil which crystallizes. Yield: 300 g (100%). MS (ES) m/z 249 [M+1]$^+$.

Preparation 6

5-(tert-Butyldimethylsilyloxy)-3-iodo-1H-indazole

Cool a solution of 5-(tert-butyldimethylsilyloxy)-1H-indazole (300.00 g, 1.21 mol) in DCM (4.00 L) to 10° C. in a 10 L jacketed reactor vessel. To the resulting solution add N-iodosuccinimide (298.89 g, 1.33 mol) in portions over 0.5 hours. Stir the mixture at RT for 3 hours to give complete conversion as indicated by liquid chromatography mass spectrometry (LC-MS) and thin layer chromatography (TLC). Cool the mixture to 10° C. and quench with water (2.5 L). Transfer the mixture to a separatory funnel and extract the aqueous layer into DCM (2.5 L). Wash the combined organic extracts with a 10% aqueous sodium thiosulfate solution (5 L) and brine. Dry the organic solution over magnesium sulfate, filter and concentrate in vacuo to afford the title compound as an orange solid. Yield: 388 g (90%). MS (ES) m/z 375 [M+1]$^+$.

Preparation 7

5-(tert-Butyldimethylsilyloxy)-3-iodo-1-(tetrahydro-2H-pyran-2-yl)-1H-indazole

Cool a solution of 5-(tert-butyldimethylsilyloxy)-3-iodo-1H-indazole (387.00 g, 1.08 mol) in DCM (2.50 L) and THF (1.00 L) to 10° C. in a 10 L jacketed reactor vessel. To the resulting mixture add methanesulfonic acid (14.0 mL, 216.02 mmol), followed by 3,4-dihydro-2H-pyran (296 mL, 3.24 mol) over 0.5 hours, observing a slight exotherm. Stir the mixture at RT for 3 hours. Cool the reaction to 10° C. and quench with saturated aqueous sodium bicarbonate (2 L). Dilute the mixture with water (2 L) and extract the aqueous layer with DCM (2 L). Wash the combined organic extracts with water (2 L) and brine. Dry the organic mixture over anhydrous sodium sulfate, filter and concentrate in vacuo. Elute the residue through a silica gel pad with eluent (0 to 10% EA/hexanes) to give the title compound. Yield: 150 g (31%). MS (ES) m/z 459 [M+1]$^+$.

Preparation 8

(E)-1-(Tetrahydro-2H-pyran-2-yl)-3-(2-(1-(2-(tetrahydro-2H-pyran-2-yloxy)ethyl)-1H-pyrazol-4-yl)vinyl)-1H-indazol-5-ol Sparge with nitrogen a mixture of 5-(tert-butyldimethylsilyloxy)-3-iodo-1-(tetrahydro-2H-pyran-2-yl)-1H-indazole (14 g, 30.54 mmol) in DMF (150 mL) in a 500 mL 3-neck round bottom flask equipped with magnetic stirring, temperature probe, and condenser with septa for 10 minutes. To the resulting solution add tributylamine (TBA, 6.7 g, 36.1 mmol) and 4,4,5,5-tetramethyl-2-vinyl-1,3,2-dioxaborolane (7.0 g, 43.18 mmol) and continue sparging for 10 minutes. To the resulting mixture add bis(triphenylphosphine) palladium (II) chloride (0.45 g, 0.63 mmol) and continue to sparge for an additional 0.5 hours. Heat the mixture at 95-100° C. for 18 hours. Cool the reaction mixture to below 40° C. and charge with 4-iodo-1-(2-(tetrahydro-2H-pyran-2-yloxy)ethyl)-1H-pyrazole (9.8 g, 30.42 mmol). To the resulting mixture add barium hydroxide octahydrate (19.3 g, 60.3 mmol) and water (13 mL) and continue sparging for 10 minutes. Add 1,1'-bis(diphenylphosphino)ferrocene palladium (II) chloride DCM complex (1.3 g, 1.56 mmol) to the reaction and continue sparging 0.5 hours. Heat the mixture at 95° C. under nitrogen for 3 hours. Dilute the mixture with EA and filter through a Celite® pad. Wash the pad with brine (400 mL) and separate the filtrate layers. Wash the organic layer with brine and extract the combined aqueous layers with EA. Combine the organic solutions and concentrate to a brown oil. Dissolve the oil in DCM (100 mL) and add to a silica gel pad. Elute the pad with eluent (50% EA in hexanes followed by 70% EA in hexanes) to afford a light brown oil. Triturate with MTBE (100 mL) to afford the title compound as a solid. Yield: 5 g (37%). MS (ES) m/z 439 [M+1]$^+$.

Preparation 9

5-((R)-1-(3,5-Dichloropyridin-4-yl)ethoxy)-1-(tetrahydro-2H-pyran-2-yl)-3-((E)-2-(1-(2-(tetrahydro-2H-pyran-2-yloxy)ethyl)-1H-pyrazol-4-yl)vinyl)-1H-indazole In a 3-neck 250 mL round bottom flask equipped with an internal temperature probe, reflux condenser, nitrogen blanket and magnetic stir bar, slurry (E)-1-(tetrahydro-2H-pyran-2-yl)-3-(2-(1-(2-(tetrahydro-2H-pyran-2-yloxy)ethyl)-1H-pyrazol-4-yl)vinyl)-1H-indazol-5-ol (10.0 g, 22.83 mmol) and cesium carbonate (7.88 g, 23.94 mmol) in ACN (92 mL) and warm to 60° C. To the suspension, add (S)-1-(3,5-dichloropyridin-4-yl)ethyl methanesulfonate (7.03 g, 26.02 mmol) and stir overnight. Cool the reaction mixture to RT, filter and wash solids with ACN. Concentrate the filtrate and purify the residue by silica gel chromatography (2-4% (2 M ammonia in methanol)/DCM). Combine product fractions and concentrate in vacuo to a white foam. Yield: 12.5 g (86%). MS (ES) m/z 612 [M+1]$^+$.

Preparation 10(The Amorphous Form)

(R)-(E)-2-(4-(2-(5-(1-(3,5-Dichloropyridin-4-yl)ethoxy)-1H-indazol-3-yl)vinyl)-1H-pyrazol-1-yl)ethanol

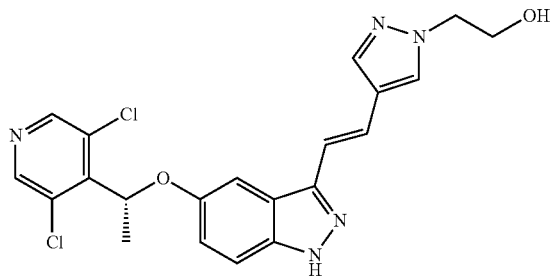 [SMILES: C[C@@H](Oc1ccc2[nH]nc(/C=C/c3cnn(CCO)c3)c2c1)c1c(Cl)cncc1Cl]

Charge a 3-neck, 250 mL round bottom flask equipped with an addition funnel, nitrogen inlet, internal temperature probe and magnetic stirrer with methanol (57 mL) and cool in an ice bath. To the resulting solution, add acetyl chloride (20 mL, 281.03 mmol) slowly through an addition funnel. To the solution, add 5-((R)-1-(3,5-dichloropyridin-4-yl)ethoxy)-1-(tetrahydro-2H-pyran-2-yl)-3-((E)-2-(1-(2-(tetrahydro-2H-pyran-2-yloxy)ethyl)-1H-pyrazol-4-yl)vinyl)-1H-indazole (7.1 g, 11.59 mmol) dissolved in methanol (40 mL) via addition funnel. After addition is complete, remove the ice bath, warm to RT and stir the mixture for 4 hours. Concentrate the reaction mixture in vacuo to a yellow foam. Dissolve the yellow foam in methanol (10 mL) and add slowly to a saturated aqueous sodium bicarbonate solution (120 mL). Stir the mixture at RT for 30 minutes. Filter the mixture, wash the solid with water (100 mL), and dry under vacuum. Recrystallize the solid from hot EA/methanol/hexanes to give the title compound as a white solid. Yield: 2.1 g (41%). MS (ES) m/z 444 [M+1]$^+$.

EXAMPLE 1

(R)-(E)-2-(4-(2-(5-(1-(3,5-Dichloropyridin-4-yl)ethoxy)-1H-indazol-3-yl)vinyl)-1H-pyrazol-1-yl)ethanol monohydrate Form 1

A reaction vessel is purged with nitrogen and charged with (R)-(E)-2-(4-(2-(5-(1-(3,5-dichloropyridin-4-yl)ethoxy)-1H-indazol-3-yl)vinyl)-1H-pyrazol-1-yl)ethanol and a solvent mixture consisting of 11% water/acetonitrile. The resulting suspension is heated to an internal temperature of 66-68° C. producing a solution. The solution is cooled slowly to 56-58° C., then seeded with a suspension of seed crystals in 11% water/acetonitrile mixture and stirred slowly. The reaction mixture is initially cooled down to 48-50° C. and then to 19-20° C. The product is isolated by filtration in the presence of nitrogen stream with a relative humidity of at least 80% passing through the solid cake. The humidity level in the nitrogen stream is then subsequently changed to 40% and the drying continued, resulting in the production of the title compound. Note that the seed crystal is similarly obtained as follows: A reaction vessel is purged with nitrogen and charged with (R)-(E)-2-(4-(2-(5-(1-(3,5-dichloropyridin-4-yl)ethoxy)-1H-indazol-3-yl)vinyl)-1H-pyrazol-1-yl)ethanol and a solvent mixture consisting of 11% water/acetonitrile. The resulting suspension is heated to an internal temperature of 70° C. producing a solution. The solution is then cooled slowly, allowed to crystallize, filtered and dried. This compound is a potent inhibitor of FGFR and may have the advantageous properties relative to the prior form of superior solid handling properties on a large scale, ease of purification by crystallization, and thermodynamic stability under conditions of pharmaceutical processing and storage.

The Compound of Example 1, XRPD

The XRPD pattern is collected using a PANalytical X'Pert™ Pro MPD PW3040 Pro diffractometer, equipped with a CuKa radiation (λ=1.54059 Å (voltage: 45 kV and amperage: 40 mA)) produced using an Optix long fine-focus source. The specimen is sandwiched between 3-micron thick films, analyzed in transmission geometry, and rotated at 1 revolution per second to optimize orientation statistics. Prior to the analysis a silicon specimen (NIST standard reference material 640c) is analyzed to verify the position of the silicon 111 peak. One Panalytical pattern is analyzed for this material, and preferred orientation and particle statistic effects are assessed through comparison of the simulated XRPD pattern from single crystal analysis. An elliptically graded multilayer mirror is used to focus the CuKa X-rays of the source through the specimen and onto the detector. Diffraction patterns are collected using a scanning position-sensitive detector (X'Celerator) located 240 mm from the specimen. Data are collected from 1.01 to 39.99 degree 2θ with a step size of 0.017 degree 2θ and a scan speed of 1.2 degree/min and with a 0.5 degree divergence slit and a 0.25 degree scattering slit. A beam-stop is used to minimize the background generated by air scattering. Soller slits are used for the incident and diffracted beams to minimize axial divergence. Observed peaks are shown in Table 1. An intensity threshold of 5% is used.

TABLE 1

Observed peaks for the Compound of Example 1, XRPD.

| °2θ | d space (Å) | Intensity (%) |
|---|---|---|
| 3.54 ± 0.10 | 24.975 ± 0.726 | 45 |
| 7.08 ± 0.10 | 12.485 ± 0.179 | 10 |
| 10.62 ± 0.10 | 8.328 ± 0.079 | 9 |
| 12.51 ± 0.10 | 7.075 ± 0.057 | 78 |
| 13.00 ± 0.10 | 6.812 ± 0.053 | 37 |
| 13.60 ± 0.10 | 6.512 ± 0.048 | 16 |
| 14.18 ± 0.10 | 6.245 ± 0.044 | 13 |
| 14.65 ± 0.10 | 6.046 ± 0.041 | 100 |
| 14.97 ± 0.10 | 5.919 ± 0.040 | 29 |
| 15.49 ± 0.10 | 5.722 ± 0.037 | 16 |
| 16.24 ± 0.10 | 5.459 ± 0.034 | 35 |
| 16.59 ± 0.10 | 5.344 ± 0.032 | 24 |
| 17.06 ± 0.10 | 5.198 ± 0.030 | 26 |
| 17.76 ± 0.10 | 4.995 ± 0.028 | 20 |
| 18.49 ± 0.10 | 4.798 ± 0.026 | 9 |
| 19.16 ± 0.10 | 4.632 ± 0.024 | 68 |
| 20.37 ± 0.10 | 4.361 ± 0.021 | 44 |
| 21.67 ± 0.10 | 4.101 ± 0.019 | 8 |
| 21.89 ± 0.10 | 4.061 ± 0.018 | 8 |
| 22.17 ± 0.10 | 4.010 ± 0.018 | 22 |
| 23.02 ± 0.10 | 3.863 ± 0.017 | 54 |
| 24.33 ± 0.10 | 3.659 ± 0.015 | 15 |
| 25.25 ± 0.10 | 3.528 ± 0.014 | 27 |
| 25.93 ± 0.10 | 3.436 ± 0.013 | 49 |
| 26.16 ± 0.10 | 3.406 ± 0.013 | 16 |
| 26.77 ± 0.10 | 3.331 ± 0.012 | 10 |
| 27.23 ± 0.10 | 3.275 ± 0.012 | 15 |
| 28.25 ± 0.10 | 3.159 ± 0.011 | 10 |
| 28.59 ± 0.10 | 3.123 ± 0.011 | 11 |
| 29.56 ± 0.10 | 3.022 ± 0.010 | 13 |

Thus, a properly prepared sample of Example 1 may be characterized by X-ray diffraction pattern using CuK$_\alpha$ radiation as having diffraction peaks (2-theta values) as described in Table 1, and in particular having peaks at 14.65 in combination with one or more of the peaks at 3.54, 12.51, and 19.16; and more particularly having a peak at 14.65; with a tolerance for the diffraction angles of 0.1 degrees, more preferably 0.01 degrees.

Aberrant regulation of the FGF/FGFR pathway has been implicated in many forms of human malignancies. FGFRs and FGFs are often over-expressed in numerous cancers, and their expression often correlates with poor prognosis. The activating mutations in the FGFR kinase domain have been found in several types of tumors, including breast, NSCLC, bladder, gastric, prostate, colon, and multiple myeloma. Genomic amplification of FGFR locus was also detected in many breast, gastric, and lung cancer patients. Over-expression of FGFRs or FGFs has also been found in many different types of tumors such as bladder, multiple myeloma, prostate, and lung cancers. Other cancers that might benefit from FGFR family pathway inhibitor therapy include AML, liver cancer, melanoma, head and neck cancer, thyroid cancer, pancreatic cancer, renal cell cancer, glioblastoma, and testicular cancer. In addition to their roles in tumor formation and progression, FGFs and FGFRs are also key regulators of angiogenesis, especially during tumor growth. The FGF/FGFR axis also plays an important role in augmenting other tumor stromal cells such as cancer associated fibroblasts. Up-regulation of FGFs also leads to resistance to anti-angiogenic and other chemo-therapies. Finally, small molecule inhibitors of FGFRs have demonstrated anti-tumor activities in several preclinical tumor models and are being explored in the clinic. Taken together, the FGF/FGFR pathway is essential to several important cellular processes in cancer cells. For these reasons, therapies based on targeting FGFRs and/or FGF signaling may affect both the tumor cells directly and tumor angiogenesis.

Preparation 10 is tested essentially as described below in the following assays: FGFR1 Enzyme Assay (Filter Binding), the FGFR3 Enzyme Assay (Filter Binding), FGF9 induced p-ERK in RT-112 cell based assay (in the presence of BSA), and the AlphaScreen SureFire Detection of ERK phosphorylation (Thr202/Tyr204) in Human Umbilical Vein Endothelial Cells (HUVEC) cell based assays. These assays demonstrate that Preparation 10 is an FGFR family pathway inhibitor and has anti-cancer activity. Thus, results with the amorphous form of (R)-(E)-2-(4-(2-(5-(1-(3,5-Dichloropyridin-4-yl)ethoxy)-1H-indazol-3-yl)vinyl)-1H-pyrazol-1-yl) ethanol are indicative of results with the compound of the present invention. Crystal forms of the compound are still advantageous because they may offer the properties relative to the prior form of superior solid handling properties on a large scale, ease of purification by crystallization, and thermodynamic stability under conditions of pharmaceutical processing and storage.

FGFR1 and FGFR3 Enzyme Assay (Filter Binding)

FGFR1 or FGFR3 kinase (0.15 ng/μL human FGFR1 or 0.32 ng/μL human FGFR3) is incubated in 50 μL of a buffer containing 10 mM 4-(2-hydroxyethyl)-1-piperazineethanesulfonic acid (HEPES) pH 7.5, 8 mM tris(hydroxymethyl)aminomethane (Tris-HCl), pH 7.5, 5.0 mM dithiothreitol (DTT), 10.0 μM adenosine triphosphate (ATP), 10 mM MnCl$_2$, 150 mM NaCl, 0.01% TRITON® X-100, 0.5 μCi $^{33}$P-ATP, and 0.05 μg/μL Poly(Glu-Tyr). The reaction is carried out in a volume of 50 μL at RT for 30 minutes and then quenched by adding 130 μL of 10% H$_3$PO$_4$. The reaction (120 μL) is transferred to a 96 well 1.0 μm glass fiber filter plate, incubated at RT for 20-30 minutes and then washed 3× on a TITERTEK® Zoom with 0.5% H$_3$PO$_4$. Wells are air dried before addition of 40 μL of MicroScint™ 20(Packard) and then counted on a Wallac Micobeta counter. For compound inhibition, the compound is provided as 10 mM stocks in dimethyl sulfoxide (DMSO). The compound is serially diluted 1:3 in 20% DMSO to create a 10 point concentration-response curve and diluted 1:5(20 μM to 0.001 μM final in 4% final DMSO concentration) into the reaction plate prior to addition of the reaction mixture in the filter plate to determine compound activity. Control wells contain 4% DMSO only while the baseline is established by control wells containing 0.1 M ethylenediaminetetraacetic acid (EDTA). The percent inhibition values for each of the 10 concentrations are calculated from control wells on each plate and the 10-point concentration response data are subsequently analyzed using ActivityBase software (IDBS) using a 4-parameter logistic equation and absolute IC$_{50}$ values estimated from the resulting curve fit. The FGFR1 and FGFR3 enzyme assays have Minimum Significant Ratios (MSR) for the estimated $IC_{50}$ of 1.38 and 1.47, respectively. The $IC_{50}$ results for Preparation 10 for FGFR1 and FGFR3 in these assays are estimated to be 0.0077 and 0.0064 µM, respectively. This data demonstrates that Preparation 10 is a potent FGFR1 and FGFR3 enzyme inhibitor.

FGF9 Induced p-ERK with BSA

Human RT112 bladder carcinoma cells are seeded at a density of 5,000 cells per well in 100 µL RPMI 1640(Gibco 11875-085) supplemented with 10% fetal bovine serum (FBS, Gibco 10082-147) and 1% of a penicillin/streptomycin solution (Gibco 15140-122) in CELLBIND® 96 well plates (Corning 3340) and incubated overnight at 37° C. The next morning the growth medium is removed and replaced with 100 µL RPMI 1640 supplemented with 20 mg/mL bovine serum albumin (BSA). After 3 hours of incubation at 37° C., 20 µL of 3× serially diluted compounds in RPMI 1640 with 20 mg/mL BSA in 6% DMSO are added to each well. This yielded a 10 point dose-response curve ranging from 10-0.005 µM in 1% DMSO. The incubation is continued for 1 hour at 37° C. The cells are stimulated with 50 µL of a 50 µg/mL FGF9(R&D Systems 273-F9) solution in serum free RPMI to give a final concentration of 500 ng/mL FGF9. Cells are fixed by the addition of 30 µL of a 25% formaldehyde solution in phosphate buffered saline (PBS) (3.7% formaldehyde final concentration), and incubated 30 minutes at RT. Cells are washed 3× with PBS, followed by the addition of 100 µL of cold methanol and incubated for 30 minutes at −20° C. The methanol is removed and the cells are treated with PBS containing 0.1% TRITON® X-100(PBST), washed 3× with PBS, and incubated 15 minutes at RT. Cells are then incubated overnight at 4° C. with gentle shaking in 50 µL of a 1:400 dilution of the p-p44/42 MAPK primary antibody (Cell Signaling 9101S) in PBS supplemented with 2% BSA, 0.01% Phosphatase Inhibitor Cocktail 1(Sigma P2850), 0.01% Phosphatase Inhibitor Cocktail 2(Sigma P5726), and 0.01% Protease Inhibitor Cocktail (Sigma P8340). The next morning, plates are washed 2× with PBST and 2× with PBS, followed by a 1 hour RT incubation in the dark in 80 uL of a 1:1000 dilution of the Alexa Fluor 488 goat anti-rabbit IgG H+L secondary antibody (Invitrogen A11034) in PBS with 1% BSA and 0.1% of Phosphatase Inhibitor Cocktail 1, 0.01% Phosphatase Inhibitor Cocktail 2, and 0.01% Protease Inhibitor Cocktail. Cells are washed 3× with PBS, followed by the addition of 100 µL of a 1:200 dilution of propidium iodide (PI) (Molecular Probe P-3566) in PBS and then incubated in the dark for 1 hour. The p-ERK positive cells and total cells per well are identified with the ACUMEN EXPLORER™ (TTP LabTech Ltd) using optical filter 500-530 nM and 575-640 nM for Alexa 488 and PI, respectively. The total mean intensity for pERK/well using the Alexa 488 values is subsequently converted to percent inhibition using values obtained from MIN (10 µM positive control compound in DMSO) and MAX (DMSO alone) controls run on the same plate. The percentage inhibition values and the 10-point concentration response data are subsequently analyzed using a 4-parameter sigmoidal dose response equation and relative $IC_{50}$ values are estimated from the resulting curve. The FGF9 induced p-ERK with BSA assay has a Minimum Significant Ratio (MSR) for the estimated $IC_{50}$ of 2.7. The $IC_{50}$ for Preparation 10 in this assay is estimated to be 0.0004 µM. This data demonstrates that Preparation 10 is a potent inhibitor of FGF9 induced ERK phosphorylation in human cancer cells.

AlphaScreen SureFire Detection of ERK Phosphorylation (Thr202/Tyr204) in Human Umbilical Vein Endothelial Cells (HUVEC)

The effect of compound on the inhibition of FGF receptor 1 is measured by monitoring the phosphorylation of ERK (pERK) in response to basic-Fibroblast growth factor (b-FGF) stimulation in Human Umbilical Endothelial cells (HUVEC). The levels of pERK formed are measured using the ALPHASCREEN® SUREFIRE® system (TGR Biosciences, TGRES50K). This is a homogeneous assay format utilizing the immuno-sandwich capture of the phosphorylated analyte followed by detection using antibody-coated ALPHASCREEN® beads (Perkin Elmer) to generate an amplified signal.

HUVEC cells are recovered and maintained in growth medium consisting of endothelial cell basal medium (Clonetics, CC-3132) supplemented with 10% FBS 0.4% bovine brain extract 0.1% hydrocortisone, 0.1% gentamicin sulfate amphotericin-B, and 0.1% epidermal growth facter, human recombination until passage 7. For the assay, cells are harvested by standard procedures and then counted. Cells (20,000/well) are plated in 100 µL of growth medium into 96 well Poly-D-Lysine coated plates (BD, 354640). Plates are incubated overnight at 37° C., 5% $CO_2$.

On the day of the assay, cells are serum starved in 100 µL EBM (endothelial cell basal) medium containing 1.5% FBS and 20 mg/mL BSA for 3 hours at 37° C., 5% $CO_2$, then treated with 20 µM of 3× serially diluted compound in starvation medium for 1 hour at 37° C. This yielded a 10 point concentration-response curve ranging from 10-0.005 µM in 1% DMSO. After 1 hour compound treatment, cells are stimulated with 50 µL b-FGF (Sigma, F0291, final b-FGF concentration 50 ng/mL) at 37° C. for 15 minutes. In the wells containing cells and 50 µL stimulator b-FGF yields MAX signal, and cells with 10 µM positive control compound and 50 µL stimulator b-FGF as MIN. The medium then is removed and 50 µL of 1× SUREFIRE® Lysis Buffer (TGR Biosciences SUREFIRE® Kit component) is added/well and incubation continued at RT for 10 minutes with gentle shaking. For pERK detection, 6 µL lysate and 10 µL reaction mixture (60 parts reaction buffer/10 parts activation buffer/ 0.6 part each of donor and acceptor beads, Perkin Elmer, 6760617R) are transferred to a 384 well proxiplate (Perkin Elmer, 6006280). The plate is sealed and incubated at RT for 2 hours with gentle shaking and then read on Perkin Elmer EnVision plate reader equipped with a TurboModule using standard ALPHASCREEN® settings ($Ex_{680\ nm}$ and $Em_{520-620\ nm}$). The emission data is converted to percent inhibition determined from MAX (DMSO alone) and MIN (10 µM positive control compound in DMSO) controls on each plate and ten-point compound concentration data are then fit to a four-parameter logistic equation using ACTIVITYBASE® 4.0 and the $IC_{50}$ is estimated. The ALPHASCREEN® SUREFIRE® Detection of ERK phosphorylation ((Thr202/Tyr204) assay has a Minimum Significant Ratio (MSR) for the $IC_{50}$ of 2.1. The $IC_{50}$ of Preparation 10 in this assay is estimated to be 0.0006 µM. This data demonstrates that Preparation 10 is a potent inhibitor of bFGF induced ERK phosphorylation in Human Umbilical Endothelial cells.

The compound of the present invention is preferably formulated as a pharmaceutical composition administered by a variety of routes. Most preferably, such compositions are for oral or intravenous administration. Such pharmaceutical compositions and processes for preparing same are well known in the art. See, e.g., REMINGTON: THE SCIENCE AND PRACTICE OF PHARMACY (D. Troy, et al., eds., 21$^{st}$ ed., Lippincott Williams & Wilkins, 2005).

The compound of the present invention is generally effective over a wide dosage range. For example, dosages per day normally fall within the range of about 0.5 to about 100 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

I claim:

1. Crystalline (R)-(E)-2-(4-(2-(5-(1-(3,5-dichloropyridin-4-yl)ethoxy)-1H-indazol-3-yl)vinyl)-1H-pyrazol- 1-yl)ethanol monohydrate.

2. The compound according to claim 1 which is isolated.

3. The compound according to claim 1 characterized by the X-ray powder diffraction pattern (Cu radiation, λ=1.54059 Å) comprising peaks at 3.54, 12.51, 14.65, 20.37, 23.02, and 19.16(2θ+/−0.1°).

4. A pharmaceutical composition comprising crystalline (R)-(E)-2-(4-(2-(5-(1-(3,5-dichloropyridin-4-yl)ethoxy)-1H-indazol-3-yl)vinyl)-1H-pyrazol-1-yl)ethanol monohydrate in combination with a pharmaceutically acceptable carrier, diluent or excipient.

5. The compound according to claim 1 characterized by the X-ray powder diffraction pattern (Cu radiation, λ=1.54059 Å) comprising peaks at 12.51, 14.65, 20.37, 23.02, and 19.16 (2θ+/−0.1°).

6. The compound according to claim 1 characterized by the X-ray powder diffraction pattern (Cu radiation, λ=1.54059 Å) comprising peaks at 12.51, 14.65, 23.02, and 19.16(2θ+/−0.1°).

7. The compound according to claim 2 characterized by the X-ray powder diffraction pattern (Cu radiation, λ=1.54059 Å) comprising peaks at 3.54, 12.51, 14.65, 20.37, 23.02, and 19.16(2θ+/−0.1°).

8. The compound according to claim 2 characterized by the X-ray powder diffraction pattern (Cu radiation, λ=1.54059 Å) comprising peaks at 12.51, 14.65, 20.37, 23.02, and 19.16 (2θ+/−0.1°).

9. The compound according to claim 2 characterized by the X-ray powder diffraction pattern (Cu radiation, λ=1.54059 Å) comprising peaks at 12.51, 14.65, 20.37, 23.02, and 19.16 (2θ+/−0.1°).

* * * * *

UNITED STATES PATENT AND TRADEMARK OFFICE
CERTIFICATE OF CORRECTION

| | | |
|---|---|---|
| PATENT NO. | : 8,530,665 B2 | Page 1 of 1 |
| APPLICATION NO. | : 13/248055 | |
| DATED | : September 10, 2013 | |
| INVENTOR(S) | : Benjamin Alan Diseroad | |

It is certified that error appears in the above-identified patent and that said Letters Patent is hereby corrected as shown below:

In The Claims

On the last page, column 12, Claim 9, line 3 please delete "20.37."

Signed and Sealed this
Twenty-third Day of December, 2014

Michelle K. Lee
*Deputy Director of the United States Patent and Trademark Office*